United States Patent [19]

Lo et al.

[11] Patent Number: 4,553,032
[45] Date of Patent: Nov. 12, 1985

[54] INFRARED ENERGY GAGE

[75] Inventors: Saukwan Lo, Fridley; Richard J. Borken, St. Louis Park, both of Minn.

[73] Assignee: Honeywell Inc., Minneapolis, Minn.

[21] Appl. No.: 431,437

[22] Filed: Sep. 30, 1982

[51] Int. Cl.⁴ ............................................. G01J 1/00
[52] U.S. Cl. .................................. 250/339; 250/343; 73/113
[58] Field of Search .................. 250/255, 338 R, 339, 250/343; 73/113

[56] References Cited

U.S. PATENT DOCUMENTS

| | | | |
|---|---|---|---|
| 3,370,502 | 2/1968 | Wilks, Jr. | 250/343 |
| 3,950,101 | 4/1976 | Dewey, Jr. | 250/341 |
| 3,997,786 | 12/1976 | Lauer et al. | 250/343 |
| 4,045,671 | 8/1977 | Dille et al. | 250/343 |
| 4,134,301 | 1/1979 | Erwin, Jr. | 73/113 |
| 4,228,192 | 10/1980 | Sanden | 250/339 |
| 4,321,465 | 3/1982 | Stover et al. | 250/255 |
| 4,323,777 | 4/1982 | Baskins et al. | 250/343 |
| 4,404,847 | 9/1983 | Larson | 73/113 |

Primary Examiner—Janice A. Howell
Attorney, Agent, or Firm—William T. Udseth

[57] ABSTRACT

Means and methods are provided for determining the energy content of a hydrocarbon fuel by infrared spectroscopy. The relationship between the energy content of the fuel and the number of carbon-carbon and carbon-hydrogen bonds in the fuel is disclosed. This relationship is utilized to determine the energy content of the hydrocarbon fuel by measuring the concentration of such carbon-carbon and carbon-hydrocarbon bonds by infrared spectroscopy. A first embodiment irradiates a hydrocarbon fuel with infrared radiation of wavelengths at which specific carbon-carbon and carbon-hydrogen bonds strongly absorb. A detector array and microprocessor process the data to compute the energy content of the fuel or rate of energy consumption by a device using the fuel. A second embodiment exposes the hydrocarbon fuel to infrared energy by using frustrated total internal reflection.

20 Claims, 2 Drawing Figures

INFRARED ENERGY GAGE

BACKGROUND OF THE INVENTION

1. FIELD OF THE INVENTION

This invention relates to devices for measuring the absorbency of infrared light by hydrocarbon fuels, and more particularly to means and methods of determining the energy content of such fuels from said absorbency.

2. PRIOR ART

Identifying petroleum by infrared absorption "signatures" is disclosed in U.S. Pat. No. 3,896,312, issued July 22, 1975 to Brown et al. Saunders in U.S. Pat No. 3,462,596, issued Aug. 19, 1969, discloses the use of an infrared source to determine the water content of fuel oils. Saunders draws a fuel sample from a supply line and the sample is confined in a low pressure zone in which the water content of the sample fuel oil is flash vaporized. The water vapor is then drawn across a beam of periodically interrupted infrared radiation containing wavelengths of radiation at which water vapor characteristically absorbs. Sarkis in U.S. Pat. No. 3,526,127 issued Sept. 1, 1970, provides a cell through which engine oil samples are passed and subjected to a broad spectrum of infrared light. A standard infrared spectrophotometer records the output. The output is passed to a comparator which compares the infrared characteristics of the oil to evaluation criteria stored in a computer. Heigel in U.S. Pat. No. 2,423,774, issued July 8, 1947, shows a system for comparing the concentration of oil in an oil well sample to a reference sample. Heigel extracts oil from the oil well sample by use of a solvent, then passes light of various wavelengths through the reference sample as well as the oil well-solvent sample. Dille in U.S. Pat. No. 4,045,671, issued Aug. 30, 1977 uses a solvent to extract oil from water and then subjects the oil-solvent sample to infrared light to thereby determine the oil content of the sample from the absorbency of the infrared light by the oil sample.

Systems where frustrated total internal reflection is employed to measure the absorbence of infrared light in materials are generally known. For example, Wilks in U.S. Pat. No. 3,370,502, issued Feb. 27, 1968, discloses a general system for identifying materials wherein a rod transparent to light wavelengths of interest, including possibly infrared light, is placed in a chamber. The material to be identified is placed in the chamber in contact with the rod and light is transmittted by total internal reflection down the rod with energy from the light beam being "diffused from" the rod "according to the material" surrounding the chamber. Harrick in U.S. Pat. No. 3,431,411 inserts a light pipe in powered solid samples and measures the amount of infrared light absorbed by the powered sample as infrared light is totally internally reflected along the light pipe. A similar system is disclosed by Sanden in U.S. Pat. No. 4,228,192, issued Oct. 14, 1980, to quantatively determine the ingredients in beer.

Not disclosed in the prior art, however, are infrared spectrographic means or methods of determining the energy content of a hydrocarbon fuel or the rate of fuel energy consumption. Such means or methods can be useful in gas furnace control, airplane turbine control or in systems for monitoring fuel quality. Improvements in engine performance and fuel efficiency can be realized with such means and methods since critical operating parameters dependent on energy content can be precisely controlled.

SUMMARY OF THE INVENTION

A hydrocarbon fuel is irradiated with an infrared light source containing light at wave numbers absorbed by certain hydrocarbon and carbon groups. For saturated hydrocarbon fuels, the groups are CH and C—C. For unsaturated or aromatic hydrocarbon fuels, the groups are C=C, C≡C and benzene. The absorbency of light at said wave numbers is used to compute the number of carbon-carbon and carbon-hydrogen bonds in the fuel. Because the number of carbon-carbon and carbon-hydrogen bonds is directly related to the heat of combustion of the fuel, the energy content of the fuel is readily provided. In conjunction with a flow meter, the rate of energy consumption of a device consuming said fuel is obtained.

A first embodiment places the fuel between an infrared emitter and an infrared detector array.

A second embodiment uses frustrated total internal reflection to expose the hydrocarbon fuel to the infrared light. A light pipe is inserted in a bypass channel which is in communication with a fuel line, and the fuel is brought into contact with the surface of the light pipe. Infrared radiation is provided in one end of the light pipe with an infrared detector array at the other end.

DESCRIPTION OF THE PREFERRED EMBODIMENT

Figure 1:
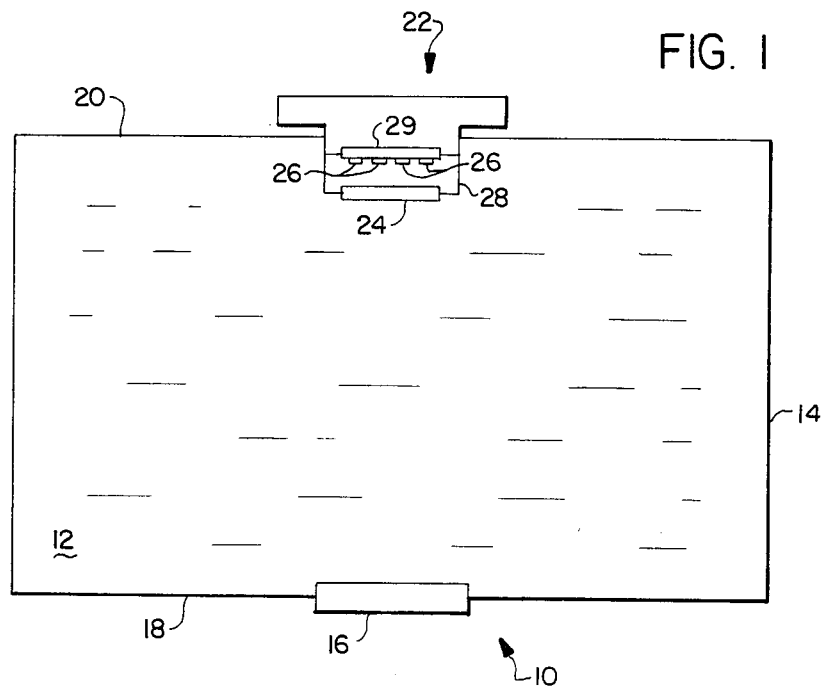
FIG. 1 is a schematic of of the first embodiment of the present invention.

The device of FIG. 1 is the first embodiment of the present invention. Therein a fuel 12 containing hydrocarbon compounds is confined in a tank 14. A source of infrared radiation 16 is provided in one side 18 of tank 14. In the other side 20 of tank 14, a means for detecting infrared radiation 22 is placed directly opposite infrared source 16.

Infrared detecting means 22 could be of various forms. If infrared source 16 is a broadband/multiband infrared source (e.g., a resistive heating filament) a plurality of bandpass filters 24 is preferably employed between source 16 and a plurality of infrared detectors 26. Bandpass filters 24 are used in conjunction with detectors 26 because variations in the light intensity reaching detectors 26 will be more easily detected if the total intensity incident on detectors 26 is reduced. Thus only light near wave numbers of interest is passed to detectors 26 by filters 24. Bandpass filters 24 can be standard dielectric material, multilayer, thin film filters.

If source 16 is precisely controlled to emit only wavelengths corresponding to wave numbers of interest, bandpass filters 24 can be deleted. Such an infrared source could be a precisely tuned laser. If bandpass filters 24 are employed, they will preferably overlie a substrate 28 which is highly transparent to infrared light. Substrate 28 could be, for example, of KRS-5 or ZnS. Infrared detectors 26 are preferably such that cooling is not a major constraint so that detecting means 22 is simplified. Polyvinylidene flouride (PVF2, a pyroelectric) is a suitable example. More sensitive solid state photodetectors (e.g., HgCdTe) could be employed of course, but at the cost of added complexity.

A semiconductor microprocessor 29 is shown as a general unit depicting the preferred mode of the invention. That is, that the intensity of the infrared radiation at wave numbers of interest which reaches detectors 26 will be automatically used to compute the amount of specified hydrocarbon and carbon groups present in fuel 12, from which the number of carbon-carbon and carbon-hydrogen bonds will be computed and the energy content of fuel 12 will directly follow. Preferably the result will be displayed continuously. The computation will involve equations set forth below.

Figure 2:
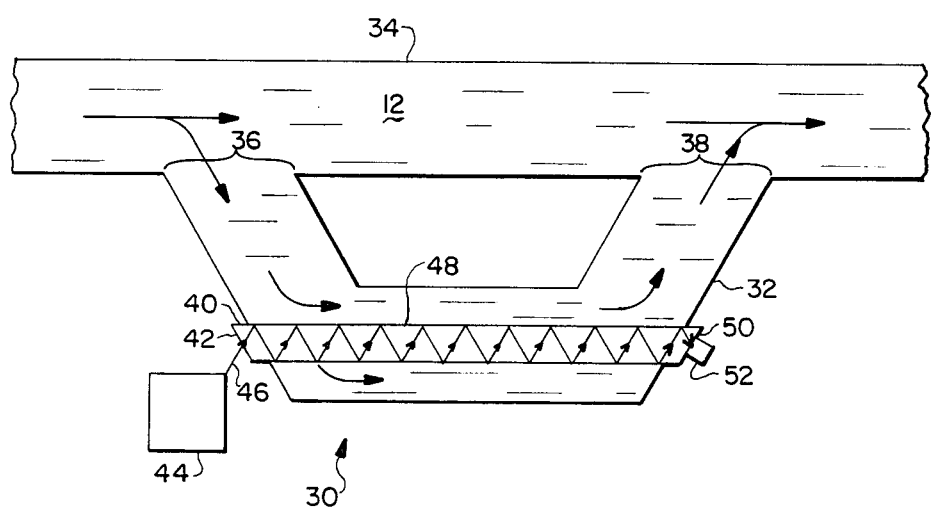
FIG. 2 is a schematic of the second embodiment of the present invention.

A second embodiment of the present invention is device 30 of FIG. 2. Device 30 includes a bypass line 32 in communication with fuel line 34 at input port 36 and output port 38. Again a hydrocarbon fuel 12 is in fuel line 34 and the arrows in FIG. 2 show fuel flow in fuel line 34 and bypass line 32.

A means for totally internally reflecting infrared light, such as light pipe 40, is provided in bypass line 32. Input face 42 of light pipe 40 is optically coupled to infrared source 44. Infrared light 46 from source 44 is adapted to strike the surface 48 of light pipe 40 at an angle such that infrared light 44 is totally internally reflected back into light pipe 40, and, by repeated total internal reflections, propogated along light pipe 40 to output face 50. Infrared light 46 is then optically coupled to detector array 52. Array 52 can have the same structure as detector means 22.

As is known, for total internal reflection the index of refraction of light pipe 40 must be greater than the index of refraction of fuel 12. Also, although light 46 is totally internally reflected the evanescent field of light 46 penetrates into the rare medium (i.e., fuel 12) with the magnitude of the electric field decaying exponentially outside of light pipe 40.

The energy content of fuel 12 is determined by first employing Beer's law in which the transmitted intensity at wavelength $\lambda$, $I(\lambda)$ is given by:

$$I(\lambda) = I_o(\lambda) e^{-\sigma nd} = I_o(\lambda) e^{-\mu d} \qquad (1)$$

where
- $I_o(\lambda)$ = incident intensity at wavelength $\lambda$
- d = optical pathlength (cm)
- $\mu$ = absorption coefficient (cm-1)
- $\sigma$ = molecular absorption cross section at wavelength $\lambda$ (cm$^2$)
- n = the number of molecules of the absorbing species per cm$^3$ If it is assumed that $\sigma$ at $\lambda$ is proportional to the number of carbon-carbon and carbon-hydrogen bonds in a material which absorb at $\lambda$ and the absorption cross-section associated with each individual bond, then one can write:

$$\mu = \sigma n = \Sigma_i \sigma_i' n_i' \qquad (2)$$

where
- $\sigma_i'$ = absorbing cross-section for bond i and
- $n_i'$ = concentration of bond i, If it is further assumed that $\sigma_i'$ is independent of the type of hydrocarbon species. By measuring the amount of absorption of light at wavelengths absorbed by each carbon-carbon and carbon-hydrocarbon bond and $\sigma$ for each bond, the concentration of energy contributing bonds can be computed. That is:

$$n_i' = 1/(\sigma_i' d) \log_e (I_o(\lambda))/I(\lambda) \qquad (3).$$

It is important that the absorption line at each $\lambda$ contributed by the various bonds is unique (or very nearly so) in order that n'i is determined accurately in equation (3). This will generally be the case since there is little overlap between the selected band absorption lines and normal contaminants (e.g. water and sulfur) in hydrocarbon fuels.

Knowing the concentrations of the various bonds, the total energy T, per unit volume can be calculated from:

$$T = \Sigma_i n_i' E_i / 10^{-3} N K cal/cm^3 \qquad (4)$$

where $E_i$ is the energy (cal. per mole) associated with bond i and N is Avogadro's number.

Note that $\sigma_i'$ can be determined by calibrating devices 10 or 30 prior to their use, or they can be obtained from tabulated values of molar extinction coefficients $\epsilon$ of the various bonds according to the formula:

$$\sigma_i' = 3.81 \times 10^{-19} \epsilon_i \qquad (5).$$

The validity of the two assumptions indicated above in connection with equations (2) and (3) is confirmed by a comparison of the energy values of the C—C, C═C, C≡C, C—H bonds and the benzene ring with the measured values of energy per mole of various hydrocarbon fuels (e.g. alkanes, alkenes, alkynes and aromatic compounds). This comparison is made assuming complete combustion from initial gas state in gaseous $H_2O$ and $CO2$ products at 25° C. and constant pressure. Such a comparison yields a maximum error of less than 0.9% for all hydrocarbons with $C_xH_y$ where x>4. Thus substantially accurate computations of T are possible with the present invention.

For saturated hydrocarbon fuels, the energy content can be sufficiently determined from the concentrations of two hydrocarbon and carbon groups, i.e. CH and C—C. The wave numbers for infrared radiation at which absorbance is perferably measured for CH and C—C are 2850-2960 cm$^{-1}$ and 1370-1390 cm$^{-1}$, respectively.

For unsaturated or aromatic hydrocarbon fuels, benzene, C═C and C≡C are the groups needed to determine the fuel energy content. The wave numbers at which absorbance is preferably measured for benzene, C═C and C≡C are 1490-1500 cm$^{-1}$, 960-980 cm$^{-1}$ and 2100-2140 cm$^{-1}$, respectively.

The infrared pathlength d is easily determined for device 10 since d is simply the distance between infrared source 16 and detector means 22. To keep tank 14 a reasonable size (i.e., on the order of several meters), the first embodiment is preferably employed when the absorption coefficients of the strongest spectral lines are approximately $10^{-2}$ cm$^{-1}$.

The pathlength d of the second embodiment must be more carefully determined than that of the first embodiment. The evanescent field will penetrate on the order of a micron into fuel 12 at each point of reflection. Thus, the total pathlength will depend on the length of pipe 40 and the angle of incidence of beam 46 with surface 48. For pathlengths from 1 to 100 microns, device 30 is particularly suitable for fuels 12 where the absorption coefficients of the strongest absorption lines are on the order of $10^3$ cm$^{-1}$.

Devices 10 and 30 can easily incorporate a temperature reference by providing a detector in detector means 22 or 52 which is not subjected to any infrared radiation from sources 16 or 46. The intensity readings of the detector means 22 and 52 can be readily compensated for any infrared radiation received by the reference detector.

The signal to noise ratio for the intensity of infrared radiation received by detector means 22 and 52 can be enhanced by electro-optically or mechanically chopping the source signals 16 or 46, and then using synchronous detection to identify source signals 16 or 46 from noise.

An alternative use of the devices of the present invention would be to distribute a series of detecting means 22 or 52 through a portion of the fuel line or tank, and thereby provide a means to determine the distribution of energy producing hydrocarbon and carbon groups in the fuel line or tank.

What is claimed is:

1. An infrared energy device for measuring the energy content of a hydrocarbon fuel, comprising:
   an infrared light source adapted to emit infrared light of incident intensity $I_o$ into said hydrocarbon fuel including wavelengths absorbed by the CH and C—C groups;
   means for detecting the absorbency of said infrared light by said groups;
   means for determining the concentration of said groups from the absorbency of said infrared light; and
   means for determining the energy content of said fuel from said concentrations.

2. The device of claim 1 wherein:
   said means for determining the absorbency of said infrared light detects transmitted light intensity I at said wavelengths absorbed by said groups;
   said means for determining the concentration of said groups generates a molecular cross section $\sigma$ for each of said groups at said wavelengths; and
   said means for determining energy content of said fuel utilizes the relationships:

$$n'_i = \frac{1}{\sigma'_i d} \log e^{\frac{I_o(\lambda)}{I(\lambda)}} \text{ and}$$

$$T = \sum_i n'_i E_i / N$$

where
   $n'_i$ = the concentration of group i bonds,
   d = optical pathlength in said fuel,
   $I_o(\lambda)$ = said infrared light's incident intensity at wavelength $\lambda$,
   $I(\lambda)$ = said infrared light's transmitted intensity at wavelength $\lambda$,
   T = total energy per unit volume,
   $E_i$ = energy per mole associated with each group and
   N = Avogadro's number.

3. The device of claim 1 wherein said infrared energy source is adapted to emit infrared energy of at least one wave number from 1370 to 1390 cm$^{-1}$ and at least one wave number from 2850 to 2960 cm$^{-1}$.

4. The device of claim 1 further including:
   means for detecting the rate of flow of said hydrocarbon fuel past said detecting means.

5. The device of claim 1 further including:
   light guide means inserted in said fuel between said infrared light source and said detecting means, which is adapted to totally internally reflect said infrared light directed therein.

6. The device of claim 1 further including means for confining at least a portion of said hydrocarbon fuel, and wherein said detecting means includes a plurality of infrared detectors positioned relative to said confining means so that the distribution of said selected groups in said confining means can be determined.

7. The device of claim 5 wherein said fuel has a first optical index of refraction and said light guide means is a light pipe having a second optical index of refraction which is larger than said first optical index of refraction.

8. The device of claim 1 wherein said detecting means includes a plurality of dielectric, multilayered, thin film bandpass filters adapted to pass infrared light of said wavelengths.

9. The device of claim 8 wherein said detecting means futher includes a substrate which is substantially transparent to infrared radiation and a plurality of pyroelectric detectors adapted to be responsive to infrared radiation, wherein said bandpass filters are on one surface of said substrate with said detectors disposed on an opposite surface of said substrate.

10. The device of claim 9 wherein said pyroelectric detectors include polyvinylidene flouride.

11. An infrared energy device for measuring the energy content of a hydrocarbon fuel, comprising:
   an infrared light source adapted to emit infrared light of incident intensity $I_o$ into said hydrocarbon fuel including wavelengths absorbed by the C═C, C≡C and benzene groups;
   means for detecting the absorbency of said infrared light by said groups;
   means for determining the concentration of said groups from the absorbency of said infrared light; and
   means for determining the energy content of said fuel from said concentrations.

12. The device of claim 11 wherein:
   said means for determining the absorbency of said infrared light detects transmitted light intensity I at said wavelengths absorbed by said groups;
   said means for determining the concentration of said groups generates a molecular cross section $\sigma$ for each of said groups at said wavelengths; and
   said means for determining energy content of said fuel utilizes the relationships:

$$n'_i = \frac{1}{\sigma'_i d} \log e^{\frac{I_o(\lambda)}{I(\lambda)}} \text{ and}$$

$$T = \sum_i n'_i E_i / N$$

where
   $n'_i$ = the concentration of group i bonds,
   d = optical pathlength in said fuel,
   $I_o(\lambda)$ = said infrared light's incident intensity at wavelength $\lambda$,
   $I(\lambda)$ = said infrared light's transmitted intensity at wavelength $\lambda$,
   T = total energy per unit volume
   $E_i$ = energy per mole associated with each group and
   N = Avogadro's number.

13. The device of claim 11 wherein said infrared energy source is adapted to emit infrared energy of at least one wave number from each of the following ranges: 960 to 980 cm$^{-1}$, 1490 to 1500 cm$^{-1}$ and 2100 to 2140 cm$^{-1}$.

14. The device of claim 11 further including:

means for detecting the rate of flow of said hydrocarbon fuel past said detecting means.

15. The device of claim 11 further including:
light guide means inserted in said fuel between said infrared light source and said detecting means, said light guide means being adapted to totally internally reflect said infrared light directed along said light guide means.

16. The device of claim 15 wherein said fuel has a first optical index of refraction and said light guide means is a light pipe having a second optical index of refraction which is larger than said first optical index of refraction.

17. The device of claim 11 further including means for confining at least a portion of said hydrocarbon fuel, and wherein said detecting means includes a plurality of infrared detectors positioned relative to said confining means so that the distribution of said selected groups in said confining means can be determined.

18. The device of claim 11 wherein said detecting means includes a plurality of dielectric, multilayered, thin film bandpass filters adapted to pass infrared light of said wavelengths.

19. The device of claim 18 wherein said detecting means further includes a substrate which is substantially transparent to infrared radiation and a plurality of pyroelectric detectors adapted to be responsive to infrared radiation, wherein said bandpass filters are on one surface of said substrate and said detectors are disposed on an opposite surface of said substrate.

20. The device of claim 19 wherein said pyroelectric detectors include polyvinylidene flouride.

* * * * *